United States Patent
Brown et al.

(10) Patent No.: US 9,500,607 B2
(45) Date of Patent: *Nov. 22, 2016

(54) GLOW DISCHARGE ION SOURCE

(71) Applicant: Micromass UK Limited, Manchester (GB)

(72) Inventors: Jeffery Mark Brown, Hyde (GB); Martin Raymond Green, Bowdon (GB); Steven Derek Pringle, Darwen (GB)

(73) Assignee: MICROMASS UK LIMITED, Wilmslow (GB)

( * ) Notice: Subject to any disclaimer, the term of this patent is extended or adjusted under 35 U.S.C. 154(b) by 146 days.

This patent is subject to a terminal disclaimer.

(21) Appl. No.: 14/063,338

(22) Filed: Oct. 25, 2013

(65) Prior Publication Data

US 2014/0051181 A1 Feb. 20, 2014

Related U.S. Application Data

(63) Continuation of application No. 13/055,612, filed as application No. PCT/GB2009/001842 on Jul. 27, 2009.

(60) Provisional application No. 61/086,213, filed on Aug. 5, 2008.

(30) Foreign Application Priority Data

Jul. 28, 2008 (GB) .................................. 0813777.0

(51) Int. Cl.
*G01N 24/00* (2006.01)
*H01J 49/00* (2006.01)
(Continued)

(52) U.S. Cl.
CPC ........... *G01N 24/00* (2013.01); *H01J 49/0009* (2013.01); *H01J 49/0072* (2013.01);
(Continued)

(58) Field of Classification Search
None
See application file for complete search history.

(56) References Cited

U.S. PATENT DOCUMENTS 5,756,994 A 5/1998 Bajic
6,373,052 B1 4/2002 Hoyes et al.
(Continued)

FOREIGN PATENT DOCUMENTS

GB WO 2006/129068 * 12/2006 ............. H01J 49/04
JP 4138650 5/1992

OTHER PUBLICATIONS

Busch, K.L., Mass Spectrometry Forum—Mass Calibration: Cluster Calibrants for Higher Masses, 2005, Mass Spectrometry Forum, retrieved from http://license.icopyright.net/user/viewFreeUse.act?fuid=MTY5MjIzMDc%3D.*

*Primary Examiner* — Robert Xu
(74) *Attorney, Agent, or Firm* — Diederiks & Whitelaw, PLC

(57) ABSTRACT

A mass spectrometer is disclosed comprising a glow discharge device within the initial vacuum chamber of the mass spectrometer. The glow discharge device may comprise a tubular electrode located within an isolation valve, which is provided in the vacuum chamber. Reagent vapor may be provided through the tubular electrode, which is then subsequently ionized by the glow discharge. The resulting reagent ions may be used for Electron Transfer Dissociation of analyte ions generated by an atmospheric pressure ion source. Other embodiments are contemplated wherein the ions generated by the glow discharge device may be used to reduce the charge state of analyte ions by Proton Transfer Reaction or may act as lock mass or reference ions.

13 Claims, 10 Drawing Sheets

(51) Int. Cl.
  *H01J 49/10* (2006.01)
  *H01J 49/12* (2006.01)
  *H01J 49/16* (2006.01)
  *H01J 49/04* (2006.01)

(52) U.S. Cl.
  CPC .......... *H01J49/0495* (2013.01); *H01J 49/107* (2013.01); *H01J 49/12* (2013.01); *H01J 49/165* (2013.01); *Y10T 436/24* (2015.01)

(56) References Cited

U.S. PATENT DOCUMENTS

| | | | |
|---|---|---|---|
| 6,570,151 | B1 | 5/2003 | Grosshans et al. |
| 6,570,152 | B1 | 5/2003 | Hoyes |
| 6,828,551 | B2 | 12/2004 | Kato |
| 6,852,971 | B2 | 2/2005 | Baba et al. |
| 7,026,610 | B2 | 4/2006 | Kato |
| 7,064,317 | B2 | 6/2006 | McLuckey et al. |
| 7,138,624 | B2 | 11/2006 | Kato |
| 7,196,326 | B2 | 3/2007 | Franzen et al. |
| 7,424,980 | B2 | 9/2008 | Ruediger et al. |
| 7,534,622 | B2 | 5/2009 | Hunt et al. |
| 7,582,862 | B2 | 9/2009 | Hartmer |
| 7,723,676 | B2 | 5/2010 | Vilkov et al. |
| 7,855,357 | B2 | 12/2010 | Truche et al. |
| 7,943,902 | B2 | 5/2011 | Ding et al. |
| 8,164,052 | B2 | 4/2012 | Wildgoose et al. |
| 8,410,437 | B2 | 4/2013 | Brown et al. |
| 2006/0255261 | A1* | 11/2006 | Whitehouse ........ H01J 49/0431 250/288 |

* cited by examiner

GLOW DISCHARGE ION SOURCE

CROSS REFERENCE TO RELATED APPLICATIONS

This application is a continuation of U.S. patent application Ser. No. 13/055,612, filed on Apr. 5, 2011, pending, which is the National Stage of International Application No. PCT/GB09/001842, filed on Jul. 27, 2009 and designating the United States, which claims benefit of and priority to Provisional Patent Application No. 61/086,213, filed Aug. 5, 2008, and United Kingdom Patent Application No. 0813777.0, filed Jul. 28, 2008. These applications are incorporated herein by reference in their entirety.

BACKGROUND OF THE INVENTION

The present invention relates to an ion source, a mass spectrometer, a method of generating ions and a method of mass spectrometry.

Electrospray ionisation ion sources are well known and may be used to convert neutral peptides eluting from an HPLC column into gas-phase analyte ions. In an aqueous acidic solution, tryptic peptides will be ionised on both the amino terminus and the side chain of the C-terminal amino acid. As the peptide ions proceed to enter a mass spectrometer the positively charged amino groups hydrogen bond and transfer protons to the amide groups along the backbone of the peptide.

It is known to fragment peptide ions by increasing the internal energy of the peptide ions through collisions with a collision gas. The internal energy of the peptide ions is increased until the internal energy exceeds the activation energy necessary to cleave the amide linkages along the backbone of the molecule. This process of fragmenting ions by collisions with a neutral collision gas is commonly referred to as Collision Induced Dissociation ("CID"). The fragment ions which result from Collision Induced Dissociation are commonly referred to as b-type and y-type fragment or product ions, wherein b-type fragment ions contain the amino terminus plus one or more amino acid residues and y-type fragment ions contain the carboxyl terminus plus one or more amino acid residues.

Other methods of fragmenting peptides are known. An alternative method of fragmenting peptide ions is to interact the peptide ions with thermal electrons by a process known as Electron Capture Dissociation ("ECD"). Electron Capture Dissociation cleaves the peptide in a substantially different manner to the fragmentation process which is observed with Collision Induced Dissociation. In particular, Electron Capture Dissociation cleaves the backbone N—$C_\alpha$ bond or the amine bond and the resulting fragment ions which are produced are commonly referred to as c-type and z-type fragment or product ions. Electron Capture Dissociation is believed to be non-ergodic i.e. cleavage occurs before the transferred energy is distributed over the entire molecule. Electron Capture Dissociation also occurs with a lesser dependence on the nature of the neighbouring amino acid and only the N-side of proline is 100% resistive to Electron Capture Dissociation cleavage.

One advantage of fragmenting peptide ions by Electron Capture Dissociation rather than by Collision Induced Dissociation is that Collision Induced Dissociation suffers from a propensity to cleave Post Translational Modifications ("PTMs") making it difficult to identify the site of modification. By contrast, fragmenting peptide ions by Electron Capture Dissociation tends to preserve Post Translational Modifications arising from, for example, phosphorytation and glycosylation.

However, the technique of Electron Capture Dissociation suffers from the significant problem that it is necessary simultaneously to confine both positive ions and electrons at near thermal kinetic energies. Electron Capture Dissociation has been demonstrated using Fourier Transform Ion Cyclotron Resonance ("FT-ICR") mass analysers which use a superconducting magnet to generate large magnetic fields. However, such mass spectrometers are very large and are prohibitively expensive for the majority of mass spectrometry users.

As an alternative to Electron Capture Dissociation it has been demonstrated that it is possible to fragment peptide ions by reacting negatively charged reagent ions with multiply charged analyte cations in a linear ion trap. The process of reacting positively charged analyte ions with negatively charged reagent ions has been referred to as Electron Transfer Dissociation ("ETD"). Electron Transfer Dissociation is a mechanism wherein electrons are transferred from negatively charged reagent ions to positively charged analyte ions. After electron transfer, the charge-reduced peptide or analyte ion dissociates through the same mechanisms which are believed to be responsible for fragmentation by Electron Capture Dissociation i.e. it is believed that Electron Transfer Dissociation cleaves the amine bond in a similar manner to Electron Capture Dissociation. As a result, the product or fragment ions which are produced by Electron Transfer Dissociation of peptide analyte ions comprise mostly c-type and z-type fragment or product ions.

One particular advantage of Electron Transfer Dissociation is that such a process is particularly suited for the identification of post-translational modifications ("PTMs") since weakly bonded PTMs like phosphorylation or glycosylation will survive the electron induced fragmentation of the backbone of the amino acid chain.

It is known to perform Electron Transfer Dissociation by mutually confining cations and anions in a 2D linear ion trap which is arranged to promote ion-ion reactions between reagent anions and analyte cations. The cations and anions are simultaneously trapped within the 2D linear ion trap by applying an auxiliary axially confining RF pseudo-potential barrier at both ends of the 2D linear quadrupole ion trap.

Another method of performing Electron Transfer Dissociation is known wherein a fixed DC axial potential is applied at both ends of a 2D linear quadrupole ion trap in order to confine ions having a certain polarity (e.g. reagent anions) within the ion trap. Ions having an opposite polarity (e.g. analyte cations) to those confined within the ion trap are then directed into the ion trap. The analyte cations will react with the reagent anions already confined within the ion trap.

It is known that when multiply charged (analyte) cations are mixed with (reagent) anions then loosely bound electrons may be transferred from the (reagent) anions to the multiply charged (analyte) cations. Energy is released into the multiply charged cations and the multiply charged cations may be caused to dissociate. However, some of the (analyte) cations may not dissociate but may instead be reduced in charge state. The cations may be reduced in charge by one of two processes. Firstly, the cations may be reduced in charge by Electron Transfer ("ET") of electrons from the anions to the cations. Secondly, the cations may be reduced in charge by Proton Transfer ("PT") of protons from the cations to the anions. Irrespective of the process, an abundance of charged reduced product ions are observed within mass spectra and give an indication of the degree of ion-ion reactions (either ET or PT) that are occurring.

In bottom-up or top-down proteomics Electron Transfer Dissociation experiments may be performed in order to maximize the information available by maximizing the abundance of dissociated product ions within mass spectra. The degree of Electron Transfer Dissociation fragmentation depends upon the conformation of the cations (and anions) together with many other instrumental factors. It can be difficult to know a priori the optimal parameters for every anion-cation combination from an LC run.

A problem with known mass spectrometers which incorporate an Electron Transfer Dissociation fragmentation cell is that the reagent anions which are used to cause analyte cations to fragment are generated by an additional ion source (e.g. an Atmospheric Pressure Chemical Ionisation ion source) which is arranged alongside an ion source (e.g. an Electrospray ion source) which is used to ionise the sample of interest. Locating two ion sources in close proximity to the inlet to the mass spectrometer is problematic. Furthermore, the known arrangement can suffer from the problem of cross-talk. A yet further problem with the known arrangement is that the reagents which are produced from the Atmospheric Pressure Chemical Ionisation ion source may be carcinogenic. Another problem with the known arrangement is that the sensitivity of the Atmospheric Pressure Chemical Ionisation ion source for generating the reagent ions is relatively low.

It is therefore desired to provide an improved mass spectrometer and an improved method of generating reagent ions for use in Electron Transfer Dissociation.

SUMMARY OF THE INVENTION

According to an aspect of the present invention there is provided a mass spectrometer comprising:

a vacuum chamber;

an atmospheric pressure ion source for generating first ions, wherein first ions generated by the atmospheric pressure ion source are transmitted, in use, into the vacuum chamber via a sampling cone or first aperture; and a glow discharge device for generating second ions, wherein second ions generated by the glow discharge device are either generated within the vacuum chamber or are transmitted into the vacuum chamber without being transmitted through the sampling cone or first aperture.

Less preferred embodiments are contemplated wherein the atmospheric pressure ion source may be substituted with a sub-atmospheric pressure ion source such as a sub-atmospheric pressure Electrospray ionisation ion source.

It will be understood by those skilled in the art that corona discharge devices and arc or spark discharge devices should not be construed as comprising "a glow discharge device" within the meaning of the present application. Typical operating parameters for glow discharge operation are that the glow discharge device is operated at sub-atmospheric pressure preferably in the range 0.01-15 mbar. The voltage applied to the pin or electrode of the glow discharge device once a glow discharge has been initiated is preferably in the range 100-2000 V and the applied current is preferably in the range 0.1 µA-100 µA. By contrast, corona discharge devices are typically operated at atmospheric (or near atmospheric) pressure i.e. at pressures >900 mbar. For a corona discharge device the applied current is typically in the range 5-15 µA and the applied voltage once a corona discharge has been established is typically in the range 3000-7000 V.

A corona discharge may be considered to comprise a gas discharge where the geometry confines the gas ionising processes to high-field ionisation region(s) around the active electrode(s). As all discharge forms have ionisation regions, the distinguishing feature of a corona discharge may be considered to be the existence of a low field drift region connecting the ionisation region(s) with the eventual low field passive electrodes. In this drift region ions and electrons drift and react with neutrals, but with too low energy to ionise and too low density to react with other ionised particles. In unipolar conduction coronas the drifting ions/electrons will be of the corona polarity (i.e. no plasma) and their space charge field will be the dominating factor in determining both the corona current/voltage characteristic and the current density distribution in the discharge gap.

In a low-density, low-temperature glow (or plasma) discharge (such as that used according to the preferred embodiment) the voltage applied to the plasma is greater than the ionisation potential of the gas used. Most of the plasma voltage drop is near the cathode where the majority of ionisation occurs. The discharge is sustained by secondary electrons emitted when ions or recombination radiation impact on the cathode. Electrons are accelerated away from the cathode and ionise neutral gas in the discharge.

The glow discharge device preferably comprises an electrode or pin and the mass spectrometer preferably further comprises a voltage device for supplying or applying a DC and/or RF voltage to the electrode or pin in order to cause or generate a glow discharge.

The mass spectrometer preferably further comprises one or more dispensing devices for dispensing one or more reagents in proximity to the glow discharge device so that the one or more reagents are ionised, in use, by a glow discharge caused or generated by the glow discharge device.

The one or more reagents preferably comprise one or more Electron Transfer Dissociation reagents and/or one or more Proton Transfer Reaction reagents and/or one or more lock mass or calibration reagents.

The glow discharge device may according to a less preferred embodiment be housed in a housing adjacent the vacuum chamber and second ions generated by the glow discharge device may pass from the housing through a second aperture into the vacuum chamber.

The mass spectrometer may comprise either a solid, powdered, partially solid or gel substance, a volatile liquid or a gas which is arranged or supplied in proximity to the glow discharge device so that ions are sputtered, extracted or otherwise released from the substance, liquid or gas. According to an embodiment the substance may comprise caesium iodide which when subjected to a glow discharge results in the release of caesium lock mass ions. Fluoranthene reagent vapour may be ionised by the preferred glow discharge device to provide reference ions according to an embodiment of the present invention.

The mass spectrometer preferably further comprises a supply device for supplying one or more reagents and/or one or more Proton Transfer Reaction reagents and/or one or more Electron Transfer Dissociation reagents and/or one or more lock mass reagents in proximity to the glow discharge device.

The mass spectrometer preferably further comprises an isolation valve arranged in the vacuum chamber. The isolation valve is preferably arranged downstream of the sampling cone or first aperture.

According to a less preferred embodiment the glow discharge device may be located upstream of the isolation valve. According to a particularly preferred embodiment the glow discharge device may be located within the isolation valve or downstream of the isolation valve. Other embodiments are contemplated wherein the glow discharge device may be located in a sub-atmospheric pressure region within a nozzle-skimmer interface of the mass spectrometer.

The isolation valve preferably comprises a first rotatable port wherein when the isolation valve is rotated to a first position then the vacuum chamber downstream of the isolation valve is in fluid communication with the sampling cone or first aperture and when the isolation valve is rotated to a second position then the vacuum chamber downstream of the isolation valve is no longer in fluid communication with the sampling cone or first aperture. The isolation valve preferably enables a vacuum to be maintained within the mass spectrometer when not in use.

The glow discharge device preferably comprises a tube having a sharpened or pointed end.

The mass spectrometer preferably further comprises a supply device for supplying one or more reagents and/or one or more Electron Transfer Dissociation reagents and/or one or more Proton Transfer Reaction reagents and/or one or more lock mass reagents through the tube.

The glow discharge device is preferably operated in a continuous or pulsed manner. According to a particularly preferred embodiment the glow discharge device is operated in a pulsed manner alternately with the analyte ion source (which preferably comprises either an atmospheric pressure ion source such as an Electrospray ion source or a sub-atmospheric pressure ion source such as a sub-atmospheric pressure Electrospray ion source).

According to an embodiment the glow discharge device is maintained or operated in use in a mode of operation at a potential selected from the group consisting of: (i) ←1 kV; (ii) −900 to −800 V; (iii) −800 to −700 V; (iv) −700 to −600 V; (v) −600 to −500 V; (vi) −500 to −400 V; (vii) −400 to −300 V; (viii) −300 to −200 V; (ix) −200 to −100 V; (x) −100 to 0 V; (xi) 0 to 100 V; (xii) 100 to 200 V; (xiii) 200 to 300 V; (xiv) 300 to 400 V; (xv) 400 to 500 V; (xvi) 500 to 600 V; (xvii) 600 to 700 V; (xviii) 700 to 800 V; (xix) 800 to 900 V; (xx) 900 to 1000 V; and (xxi) >1 kV.

According to an embodiment the glow discharge device is operated, in use, at a pressure selected from the group consisting of (i) >0.001 mbar; (ii) >0.01 mbar; (iii) >0.1 mbar (iv) >1 mbar, (v) >10 mbar; (vi) >100 mbar; (vii) <0.001 mbar; (viii) <0.01 mbar, (ix) <0.1 mbar, (x) <1 mbar; (xi) <10 mbar; (xii) <100 mbar; (xiii) 0.001-0.01 mbar; (xiv) 0.01-0.1 mbar; (xiv) 0.1-1 mbar; (xv) 1-10 mbar; and (xvi) 10-100 mbar. According to the preferred embodiment the glow discharge device is maintained at a pressure in the range 0.01-20 mbar.

The mass spectrometer preferably further comprises an Electron Transfer Dissociation fragmentation cell arranged in a second vacuum chamber, wherein the second vacuum chamber is located downstream of the vacuum chamber and wherein, in use, at least some Electron Transfer Dissociation reagent ions generated by the glow discharge device are caused to interact with at least some analyte ions within the Electron Transfer Dissociation fragmentation cell so as to cause at least some of the analyte ions to fragment by Electron Transfer Dissociation.

According to another aspect of the present invention there is provided a method of mass spectrometry comprising:
providing a vacuum chamber;
providing an atmospheric pressure ion source for generating first ions;
generating first ions by the atmospheric pressure ion source and transmitting the first ions into the vacuum chamber via a sampling cone or first aperture;
providing a glow discharge device for generating second ions; and
generating second ions by the glow discharge device, wherein the second ions are generated either within the vacuum chamber or are transmitted into the vacuum chamber without being transmitted through the sampling cone or first aperture.

According to another aspect of the present invention there is provided a mass spectrometer comprising:
an atmospheric pressure ion source for generating analyte ions; and
a glow discharge device for generating reagent ions and/or reference ions, wherein the glow discharge device is located within a vacuum chamber of the mass spectrometer.

The glow discharge device is preferably maintained at sub-atmospheric pressure. According to an embodiment of the present invention the glow discharge device is maintained at a pressure <200 mbar, further preferably <100 mbar.

The mass spectrometer preferably further comprises:
(i) an Electron Transfer Dissociation reaction cell wherein reagent ions are caused to interact with analyte ions within the reaction cell in order to cause at least some of the analyte ions to fragment by Electron Transfer Dissociation; and/or
(ii) a Proton Transfer Reaction reaction cell wherein reagent ions are caused to interact with analyte ions within the reaction cell in order to reduce the charge state of at least some of the analyte ions by Proton Transfer Reaction.

According to another aspect of the present invention there is provided a method of mass spectrometry comprising:
providing an atmospheric pressure ion source for generating analyte ions; and
using a glow discharge device for generating reagent ions and/or reference ions, wherein the glow discharge device is located within a vacuum chamber of the mass spectrometer.

The method preferably further comprises:
(i) causing reagent ions to interact with analyte ions within an Electron Transfer Dissociation reaction cell in order to cause at least some of the analyte ions to fragment by Electron Transfer Dissociation; and/or
(ii) causing the reagent ions to interact with analyte ions within a Proton Transfer Reaction reaction cell in order to reduce the charge state of at least some of the analyte ions by Proton Transfer Reaction.

According to another aspect of the present invention there is provided a mass spectrometer comprising:
an atmospheric pressure ion source for generating analyte ions;
a vacuum chamber;
a nozzle-skimmer interface separating the vacuum chamber from the atmospheric pressure ion source, wherein at least some analyte ions generated by the atmospheric pressure ion source are transmitted, in use, through the nozzle-skimmer interface into the vacuum chamber;
an isolation valve located in the vacuum chamber;
a glow discharge device for generating reagent ions and/or reference ions, wherein the glow discharge device is located within or downstream of the isolation valve; and
a device for supplying reagent to the glow discharge device.

The device preferably comprises a device for supplying reagent vapour to the glow discharge device. According to a particularly preferred embodiment the reagent vapour may be supplied through a hollow tube which forms the glow discharge device.

According to another aspect of the present invention there is provided a method of mass spectrometry comprising:

providing an atmospheric pressure ion source for generating analyte ions;

providing a vacuum chamber;

providing a nozzle-skimmer interface separating the vacuum chamber from the atmospheric pressure ion source wherein at least some analyte ions generated by the atmospheric pressure ion source are transmitted through the nozzle-skimmer interface into the vacuum chamber;

providing an isolation valve located in the vacuum chamber;

generating reagent ions and/or reference ions using a glow discharge device, wherein the glow discharge device is located within or downstream of the isolation valve; and supplying reagent to the glow discharge device.

According to another aspect of the present invention there is provided a mass spectrometer comprising:

a vacuum chamber;

a sub-atmospheric pressure ion source for generating analyte ions; and a glow discharge device for generating reagent or reference ions, wherein the reagent or reference ions generated by the glow discharge device are generated within the vacuum chamber.

According to another aspect of the present invention there is provided a method of mass spectrometry comprising:

providing a vacuum chamber;

generating analyte ions using a sub-atmospheric pressure ion source; and using a glow discharge device to generate reagent or reference ions, wherein the reagent or reference ions generated by the glow discharge device are generated within the vacuum chamber.

According to another aspect of the present invention there is provided a mass spectrometer comprising:

an atmospheric or sub-atmospheric pressure ion source for generating analyte ions;

a vacuum chamber;

a nozzle-skimmer interface separating the vacuum chamber from the ion source wherein at least some analyte ions generated by the ion source are transmitted, in use, through the nozzle-skimmer interface into the vacuum chamber;

a glow discharge device for generating reagent ions and/or reference ions, wherein the glow discharge device is located within or downstream of the nozzle-skimmer interface and is maintained in use at a sub-atmospheric pressure; and a device for supplying reagent vapour to the glow discharge device.

According to another aspect of the present invention there is provided a method of mass spectrometry comprising:

providing an atmospheric or sub-atmospheric pressure ion source for generating analyte ions;

providing a vacuum chamber;

providing a nozzle-skimmer interface separating the vacuum chamber from the ion source wherein at least some analyte ions generated by the ion source are transmitted through the nozzle-skimmer interface into the vacuum chamber;

generating reagent ions and/or reference ions using a glow discharge device, wherein the glow discharge device is located within or downstream of the nozzle-skimmer interface and is maintained at a sub-atmospheric pressure; and supplying reagent vapour to the glow discharge device.

According to another aspect of the present invention there is provided a mass spectrometer comprising:

an atmospheric pressure ion source for generating analyte ions;

a first vacuum chamber;

a nozzle-skimmer interface separating the first vacuum chamber from the ion source wherein at least some analyte ions generated by the ion source are transmitted, in use, through the nozzle-skimmer interface into the first vacuum chamber;

a glow discharge device for generating Electron Transfer Dissociation reagent ions, wherein the glow discharge device is located within or downstream of the nozzle-skimmer interface and within the first vacuum chamber wherein the glow discharge device is maintained in use at a pressure in the range 0.01-100 mbar;

a device for supplying reagent vapour to the glow discharge device so that Electron Transfer Dissociation reagent ions are formed in use by the glow discharge device; and an Electron Transfer Dissociation fragmentation cell arranged in a second vacuum chamber, wherein the second vacuum chamber is located downstream of the first vacuum chamber and wherein, in use, at least some of the Electron Transfer Dissociation reagent ions are caused to interact with at least some analyte ions within the Electron Transfer Dissociation fragmentation cell so as to cause at least some of the analyte ions to fragment by Electron Transfer Dissociation.

According to another aspect of the present invention there is provided a method of mass spectrometry comprising:

providing an atmospheric pressure ion source for generating analyte ions;

providing a first vacuum chamber;

providing a nozzle-skimmer interface separating the first vacuum chamber from the ion source;

transmitting at least some analyte ions generated by the ion source through the nozzle-skimmer interface into the first vacuum chamber;

using a glow discharge device to generate Electron Transfer Dissociation reagent ions, wherein the glow discharge device is located within or downstream of the nozzle-skimmer interface and within the first vacuum chamber;

maintaining the glow discharge device at a pressure of 0.01-100 mbar;

supplying reagent vapour to the glow discharge device so that Electron Transfer Dissociation reagent ions are formed by the glow discharge device;

providing an Electron Transfer Dissociation fragmentation cell arranged in a second vacuum chamber, wherein the second vacuum chamber is located downstream of the first vacuum chamber; and causing at least some of the Electron Transfer Dissociation reagent ions to interact with at least some analyte ions within the Electron Transfer Dissociation fragmentation cell so that at least some of the analyte ions are caused to fragment by Electron Transfer Dissociation.

According to another aspect of the present invention there is provided a computer program executable by the control system of a mass spectrometer comprising a vacuum chamber, an atmospheric pressure ion source for generating first ions and a glow discharge device for generating second ions, the computer program being arranged to cause the control system:

(i) to cause first ions generated by the atmospheric pressure ion source to be transmitted into the vacuum chamber via a sampling cone or first aperture; and (ii) to cause second ions to be generated by the glow discharge device wherein the second ions are either generated within the vacuum chamber or are transmitted into the vacuum chamber without being transmitted through the sampling cone or first aperture.

According to another aspect of the present invention there is provided a computer program executable by the control system of a mass spectrometer comprising an atmospheric pressure ion source and a glow discharge device located within a vacuum chamber of the mass spectrometer, the computer program being arranged to cause the control system:

(i) to cause the atmospheric pressure ion source to generate analyte ions; and (ii) to cause the glow discharge device to generate reagent ions and/or reference ions.

According to another aspect of the present invention there is provided a computer program executable by the control system of a mass spectrometer comprising an atmospheric pressure ion source for generating analyte ions, a vacuum chamber, a nozzle-skimmer interface separating the vacuum chamber from the atmospheric pressure ion source, an isolation valve located in the vacuum chamber, a glow discharge device, wherein the glow discharge device is located within or downstream of the isolation valve and a device for supplying reagent to the glow discharge device, the computer program being arranged to cause the control system:

(i) to cause at least some analyte ions generated by the atmospheric pressure ion source to be transmitted through the nozzle-skimmer interface into the vacuum chamber; and (ii) to cause the glow discharge device to generate reagent ions and/or reference ions.

According to another aspect of the present invention there is provided a computer program executable by the control system of a mass spectrometer comprising a vacuum chamber, a sub-atmospheric pressure ion source for generating analyte ions and a glow discharge device, the computer program being arranged to cause the control system:

(i) to cause the glow discharge device to generate reagent or reference ions within the vacuum chamber.

According to another aspect of the present invention there is provided a computer program executable by the control system of a mass spectrometer comprising an atmospheric or sub-atmospheric pressure ion source for generating analyte ions, a vacuum chamber, a nozzle-skimmer interface separating the vacuum chamber from the ion source, a glow discharge device for generating reagent ions and/or reference ions, wherein the glow discharge device is located within or downstream of the nozzle-skimmer interface and a device for supplying reagent vapour to the glow discharge device, the computer program being arranged to cause the control system:

(i) to cause at least some analyte ions generated by the ion source to be transmitted through the nozzle-skimmer interface into the vacuum chamber, and (ii) to maintain the glow discharge device at a sub-atmospheric pressure.

According to another aspect of the present invention there is provided a computer program executable by the control system of a mass spectrometer comprising an atmospheric pressure ion source for generating analyte ions, a first vacuum chamber, a nozzle-skimmer interface separating the first vacuum chamber from the ion source, a glow discharge device for generating Electron Transfer Dissociation reagent ions, wherein the glow discharge device is located within or downstream of the nozzle-skimmer interface and within the first vacuum chamber, a device for supplying reagent vapour to the glow discharge device so that Electron Transfer Dissociation reagent ions are formed by the glow discharge device and an Electron Transfer Dissociation fragmentation cell arranged in a second vacuum chamber, wherein the second vacuum chamber is located downstream of the first vacuum chamber, the computer program being arranged to cause the control system:

(i) to cause at least some analyte ions generated by the ion source to be transmitted through the nozzle-skimmer interface into the first vacuum chamber;

(ii) to maintain the glow discharge device at a pressure in the range of 0.01-100 mbar, and (iii) to cause at least some of the Electron Transfer Dissociation reagent ions to interact with at least some analyte ions within the Electron Transfer Dissociation fragmentation cell so as to cause at least some of the analyte ions to fragment by Electron Transfer Dissociation.

According to another aspect of the present invention there is provided a computer readable medium comprising computer executable instructions stored on the computer readable medium, the instructions being arranged to be executable by a control system of a mass spectrometer a vacuum chamber, an atmospheric pressure ion source for generating first ions and a glow discharge device for generating second ions, the computer program being arranged to cause the control system:

(i) to cause first ions generated by the atmospheric pressure ion source to be transmitted into the vacuum chamber via a sampling cone or first aperture; and (ii) to cause second ions to be generated by the glow discharge device wherein the second ions are either generated within the vacuum chamber or are transmitted into the vacuum chamber without being transmitted through the sampling cone or first aperture.

According to another aspect of the present invention there is provided a computer readable medium comprising computer executable instructions stored on the computer readable medium, the instructions being arranged to be executable by a control system of a mass spectrometer comprising an atmospheric pressure ion source and a glow discharge device located within a vacuum chamber of the mass spectrometer, the computer program being arranged to cause the control system:

(i) to cause the atmospheric pressure ion source to generate analyte ions; and (ii) to cause the glow discharge device to generate reagent ions and/or reference ions.

According to another aspect of the present invention there is provided a computer readable medium comprising computer executable instructions stored on the computer readable medium, the instructions being arranged to be executable by a control system of a mass spectrometer comprising an atmospheric pressure ion source for generating analyte ions, a vacuum chamber, a nozzle-skimmer interface separating the vacuum chamber from the atmospheric pressure ion source, an isolation valve located in the vacuum chamber, a glow discharge device, wherein the glow discharge device is located within or downstream of the isolation valve and a device for supplying reagent to the glow discharge device, the computer program being arranged to cause the control system:

(i) to cause at least some analyte ions generated by the atmospheric pressure ion source to be transmitted through the nozzle-skimmer interface into the vacuum chamber; and (ii) to cause the glow discharge device to generate reagent ions and/or reference ions.

According to another aspect of the present invention there is provided a computer readable medium comprising computer executable instructions stored on the computer readable medium, the instructions being arranged to be executable by a control system of a mass spectrometer comprising a vacuum chamber, a sub-atmospheric pressure ion source for generating analyte ions and a glow discharge device, the computer program being arranged to cause the control system:

(i) to cause the glow discharge device to generate reagent or reference ions within the vacuum chamber.

According to another aspect of the present invention there is provided a computer readable medium comprising computer executable instructions stored on the computer readable medium, the instructions being arranged to be executable by a control system of a mass spectrometer comprising an atmospheric or sub-atmospheric pressure ion source for generating analyte ions, a vacuum chamber, a nozzle-skimmer interface separating the vacuum chamber from the ion source, a glow discharge device for generating reagent ions and/or reference ions, wherein the glow discharge device is located within or downstream of the nozzle-skimmer interface and a device for supplying reagent vapour to the glow discharge device, the computer program being arranged to cause the control system:

(i) to cause at least some analyte ions generated by the ion source to be transmitted through the nozzle-skimmer interface into the vacuum chamber, and (ii) to maintain the glow discharge device at a sub-atmospheric pressure.

According to another aspect of the present invention there is provided a computer readable medium comprising computer executable instructions stored on the computer readable medium, the instructions being arranged to be executable by a control system of a mass spectrometer comprising an atmospheric pressure ion source for generating analyte ions, a first vacuum chamber, a nozzle-skimmer interface separating the first vacuum chamber from the ion source, a glow discharge device for generating Electron Transfer Dissociation reagent ions, wherein the glow discharge device is located within or downstream of the nozzle-skimmer interface and within the first vacuum chamber, a device for supplying reagent vapour to the glow discharge device so that Electron Transfer Dissociation reagent ions are formed by the glow discharge device and an Electron Transfer Dissociation fragmentation cell arranged in a second vacuum chamber, wherein the second vacuum chamber is located downstream of the first vacuum chamber, the computer program being arranged to cause the control system:

(i) to cause at least some analyte ions generated by the ion source to be transmitted through the nozzle-skimmer interface into the first vacuum chamber;

(ii) to maintain the glow discharge device at a pressure in the range of 0.01-100 mbar; and (iii) to cause at least some of the Electron Transfer Dissociation reagent ions to interact with at least some analyte ions within the Electron Transfer Dissociation fragmentation cell so as to cause at least some of the analyte ions to fragment by Electron Transfer Dissociation.

The computer readable medium is preferably selected from the group consisting of: (i) a ROM; (ii) an EAROM; (iii) an EPROM; (iv) an EEPROM; (v) a flash memory; (vi) an optical disk; (vii) a RAM; and (viii) a hard disk drive.

According to a preferred embodiment of the present invention a multi-purpose glow discharge device or ion source is provided. According to an embodiment reagent ions are generated by the glow discharge ion source within a vacuum chamber of the mass spectrometer. The reagent ions are preferably generated within the main body of the mass spectrometer and advantageously the glow discharge source preferably does not interfere with the positioning or operation of an atmospheric pressure ion source which is preferably used to generate analyte ions.

The reagent ions which are generated by the glow discharge ion source are preferably transmitted from the vacuum chamber or housing in which they are generated to a collision cell which is preferably arranged in a downstream vacuum chamber of the mass spectrometer. The reagent ions are preferably interacted with analyte ions within the collision cell. The analyte ions are preferably caused to fragment by ion-ion reaction with the reagent ions by a process of Electron Transfer Dissociation (ETD). The analyte ions may also be reduced in charge state by Proton Transfer Reactions (PTR) either within the collision cell or within a further collision cell.

The glow discharge ion source may additionally or alternatively be used to provide ions for calibration or lock mass correction.

According to an aspect of the present invention there is provided a mess spectrometer comprising an atmospheric pressure ion source and a glow discharge source which is preferably provided or maintained at an intermediate or sub-atmospheric pressure. The glow discharge source is preferably used to generate reagent ions. The reagent ions may be used within a reaction cell of a mass spectrometer to induce dissociation or fragmentation of organic analyte ions by Electron Transfer Dissociation.

The glow discharge source may also be used to generate reference ions. The reference ions may be used, for example, to calibrate the mass scale of the mass spectrometer or may be used to correct the calibration of the mass scale of the mass spectrometer.

The glow discharge source is preferably arranged to be operated at a pressure: (i) <100 mbar; (ii) <50 mbar (iii) <20 mbar, (iv) <10 mbar (v) <5 mbar; (vi) <2 mbar (vii) <1 mbar; (viii) <0.5 mbar; (ix) <0.2 mbar; or (x) <0.1 mbar.

The glow discharge source may be arranged to operate at a pressure: (i) 1-100 mbar; (ii) 0.5-50 mbar; (iii) 0.2-20 mbar; (iv) 0.1-10 mbar; (v) 0.1-100 mbar; (vi) 0.2-50 mbar; (vii) 0.5-20 mbar; (viii) 1-10 mbar; or (ix) 2-5 mbar.

The glow discharge source preferably comprises an electrode which is preferably held at a potential (preferably with respect to its surrounding chamber) of: (i) >50 V; (ii) >100 V; (iii) >200 V; (iv) >500 V; (v) >1000 V; (vi) <1000 V; (vii) <500 V; (viii) <200 V; (ix) <100 V; (x) 50-1000 V; and (xi) 100-500 V.

The glow discharge ion source may be operated substantially simultaneously or alternately with an Atmospheric Pressure Ionisation ion source. The Atmospheric Pressure Ionisation ion source is preferably operated at substantially atmospheric pressure.

Further embodiments are contemplated wherein the ion source which is used to generate analyte ions may comprise a sub-atmospheric pressure ion source such as a sub-atmospheric pressure Electrospray ion source. The sub-atmospheric pressure ion source used to generate analyte ions may be operated at a pressure: (i) <100 mbar, (ii) <50 mbar; (iii) <20 mbar, (iv) <10 mbar; (v) <5 mbar; (vi) <2 mbar; (vii) <1 mbar; (viii) <0.5 mbar; (ix) <0.2 mbar; (x) <0.1 mbar; or (xi) <800 mbar. The sub-atmospheric pressure ion source may be arranged to operate at a pressure: (i) 1-100 mbar; (ii) 0.5-50 mbar; (iii) 0.2-20 mbar; (iv) 0.1-10 mbar; (v) 0.1-100 mbar; (vi) 0.2-50 mbar; (vii) 0.5-20 mbar; (viii)

1-10 mbar; (ix) 2-5 mbar, or (x) 100-800 mbar. According to an embodiment the sub-atmospheric pressure ion source may be operated at a higher (or lower) pressure than that of the glow discharge ion source.

The Atmospheric Pressure Ionisation ion source may, for example, comprise an Electrospray ion source, an APCI ion source, an APPI ion source, a DESI ion source, a DART ion source or an Atmospheric Pressure MALDI ion source.

The mass spectrometer or mass analyser may comprise either a quadrupole mass analyser, 3D or Paul ion trap mass analyser, 2D or linear ion trap mass analyser, a Time of Flight mass analyser, an orthogonal acceleration Time of Flight mass analyser, a magnetic sector mass analyser, a Fourier Transform mass spectrometer ("FT-MS"), a Fourier Transform ion Cyclotron Resonance ("FT-ICR") mass analyser, a Fourier Transform electrostatic ion trap, or an orbitrap (RTM) mass analyser.

The operating pressure of the mass spectrometer is preferably arranged to be: (i) $<10^{-3}$ mbar; (ii) $<10^{-4}$ mbar; (iii) $<10^{-5}$ mbar; (iv) $<10^{-6}$ mbar; (v) $<10^{-7}$ mbar; (vi) $<10^{-8}$ mbar, (vii) $<10^{-9}$ mbar; or (viii) $<10^{-10}$ mbar.

The mass spectrometer preferably includes a gas collision cell. The gas collision cell may be used to induce decomposition or fragmentation of organic analyte ions by collision with gas molecules, interaction with electrons, interaction with reagent ions, interaction with negatively charged reagent ions, interaction with metastable atoms, interaction with metastable molecules, or interaction with metastable ions.

According to an embodiment the mass spectrometer may comprise one or more ion sources selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) a sub-atmospheric pressure Electrospray ionisation ion source; and (xxii) a Direct Analysis in Real Time ("DART") ion source.

The mass spectrometer may comprise one or more continuous or pulsed ion sources.

The mass spectrometer may comprise one or more ion guides.

According to an embodiment the mass spectrometer may further comprise one or more ion mobility separation devices and/or one or more Field Asymmetric Ion Mobility Spectrometer devices.

The mass spectrometer may comprise one or more ion traps or one or more ion trapping regions.

According to an embodiment the mass spectrometer may further comprise one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an Infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device.

According to an embodiment the mass spectrometer may comprise a mass analyser selected from the group consisting of: (i) a quadrupole mass analyser, (ii) a 2D or linear quadrupole mass analyser, (iii) a Paul or 3D quadrupole mass analyser; (iv) a Penning trap mass analyser, (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser; (x) a Fourier Transform electrostatic or orbitrap mass analyser; (xi) a Fourier Transform mass analyser; (xii) a Time of Flight mass analyser (xiii) an orthogonal acceleration Time of Flight mass analyser; and (xiv) a linear acceleration Time of Flight mass analyser.

According to an embodiment the mass spectrometer may further comprise one or more energy analysers or electrostatic energy analysers.

According to an embodiment the mass spectrometer may further comprise one or more ion detectors.

According to an embodiment the mass spectrometer may further comprise one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter, (vii) a Time of Flight mass filter; and (viii) a Wein filter.

According to an embodiment the mass spectrometer may further comprise a device or ion gate for pulsing ions.

According to an embodiment the mass spectrometer may further comprise a device for converting a substantially continuous ion beam into a pulsed ion beam.

According to an embodiment the mass spectrometer may comprise a C-trap and an orbitrap mass analyser comprising an outer barrel-like electrode and a coaxial inner spindle-like electrode, wherein in a first mode of operation ions are transmitted to the C-trap and are then injected into the orbitrap mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the orbitrap mass analyser.

According to an embodiment the mass spectrometer may comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

BRIEF DESCRIPTION OF THE DRAWINGS

Various embodiments of the present invention will now be described, by way of example only, and with reference to the accompanying drawings in which.

DETAILED DESCRIPTION OF THE PREFERRED EMBODIMENTS

Figure 1:
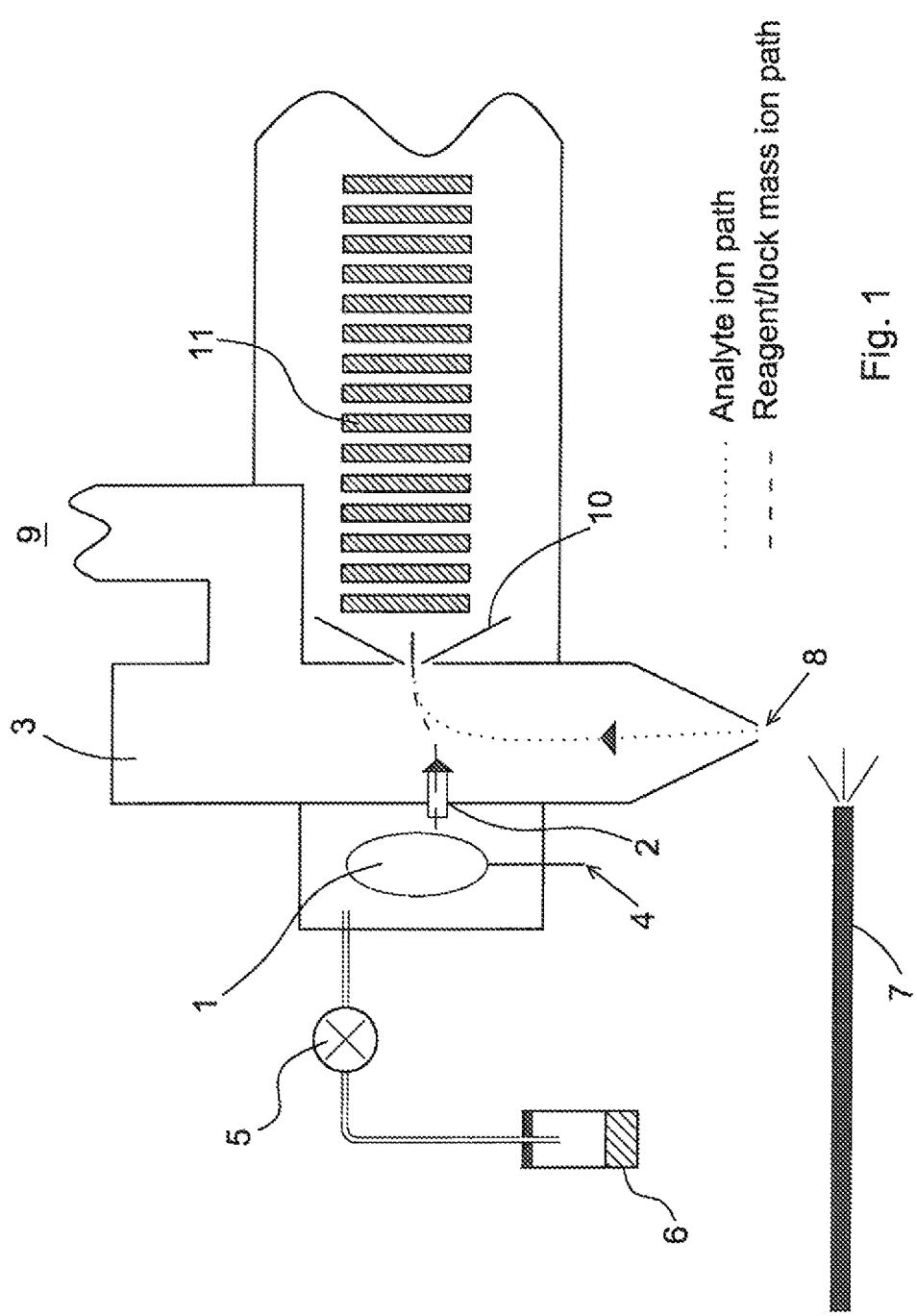
FIG. 1 shows an embodiment of the present invention wherein a glow discharge ion source for generating reagent ions is provided in a housing adjacent to the first vacuum chamber of a mass spectrometer.

An embodiment of the present invention will now be described with reference to FIG. 1 which shows an atmospheric pressure Electrospray ionisation ion source 7 arranged adjacent to the inlet and sample cone 8 of a mass spectrometer. A glow discharge source comprising an electrode or pin 4 is preferably provided in a housing adjacent to a first vacuum chamber 3 of the mass spectrometer. The electrode or pin 4 is preferably connected to an external high voltage supply. The housing is preferably maintained at a relatively high or intermediate pressure and the application of a relatively high voltage to the electrode or pin 4 preferably causes a glow discharge 1 to occur within the housing.

A volatile reagent 6 is preferably fed into the housing and is preferably injected into the glow discharge volume 1 which is preferably formed within the housing. The flow of reagent 6 is preferably controlled by a valve or micro-dosing device 5. When a high voltage is applied to the discharge electrode or pin 4 a glow discharge is preferably initiated which preferably ionises the reagent which is fed into the housing so that a plurality of reagent ions are formed within the housing. According to an embodiment a means of enhancing the extraction of reagent ions from the glow discharge volume 1 or otherwise from the housing into the first vacuum chamber 3 via an aperture 2 is preferably provided. For example, an electric field may be maintained between the housing and the first vacuum chamber 1 in order to urge reagent ions from the housing into the first vacuum chamber 1. Additional pumping (not shown) may be provided to the housing in which the glow discharge volume 1 is generated in order to minimise the flow of neutral reagent molecules from the housing via the aperture 2 into the first vacuum chamber 3 and the other ion optic sections of the mass spectrometer. Reagent ions which are generated within the housing and which pass via the aperture 2 into the first vacuum chamber 3 are then preferably onwardly transmitted through an extraction cone 10 into a second vacuum chamber. The second vacuum chamber preferably comprises an ion guide 11 which is preferably arranged to transmit ions through the second vacuum chamber. The reagent ions (preferably reagent anions) are then preferably onwardly transmitted to a collision cell (not shown) located in a further vacuum chamber downstream of the second vacuum chamber.

According to a preferred embodiment of the present invention the reagent ions which are created within the housing and which are preferably onwardly transmitted to the collision cell are preferably caused to interact with analyte ions (preferably analyte cations). The reagent ions are preferably caused to interact with analyte ions so as to cause the analyte ions to fragment by a process of Electron Transfer Dissociation ("ETD") so that a plurality of fragment, daughter or product ions are formed as a result of the Electron Transfer Dissociation process. According to another less preferred embodiment the reagent ions which are generated may be reacted with analyte ions in order to reduce the charge state of the analyte ions by Proton Transfer Reaction without substantially fragmenting the analyte ions.

According to an alternative or additional embodiment, the glow discharge ion source 1 may act as a source of ions which are preferably used for mass calibration of the mass spectrometer. A particularly preferred aspect of the present invention is that a glow discharge ion source located within the body of the mass spectrometer may be used to generate both reagent ions for use in an Electron Transfer Dissociation and/or Proton Transfer Reaction cell and also calibration or lock mass ions for calibrating the mass spectrometer.

The glow discharge source is preferably operated in a pulsed manner wherein a high voltage pulse is preferably only applied to the electrode or discharge pin 4 during a lock mass cycle or during a reagent introduction cycle. A lock mass compound is preferably only admitted into the housing during a lock mass cycle. Likewise, a reagent is preferably only admitted into the housing during a reagent introduction cycle.

Analyte ions are preferably generated by a separate atmospheric pressure ion source such as an Electrospray Ionisation ion source 7 as shown in FIG. 1. The ion source for generating analyte ions is preferably external to the main body of the mass spectrometer.

A known conventional mass spectrometer comprises two ion sources. The first ion source comprises an Electrospray ion source for generating analyte ions and the second ion source comprises an Atmospheric Pressure Chemical Ionisation ion source for generating reagent ions or calibration ions. The necessity to use two atmospheric pressure ion sources is problematic and makes the ion source geometry relatively complex. The two ion sources can also interfere with each other and can cause problems due to cross-talk. The preferred embodiment is therefore particularly advantageous in that only a single Electrospray ion source needs to be provided. This simplifies the ion source geometry and removes any problem of cross-talk between ion sources.

A particularly serious problem with known mass spectrometers is that many of the reagents which are ionised to produce reagent ions for use in Electron Transfer Dissociation such as azobenzene are carcinogenic. An important advantage therefore of the preferred embodiment is that reagents which are used to generate reagent ions are not sprayed or otherwise emitted external to the inlet aperture of the mass spectrometer (and hence in the vicinity of a user) but instead are sprayed or otherwise injected internally within a vacuum chamber of the mass spectrometer. As a result, the exposure of a user to potentially carcinogenic reagents is significantly reduced.

A yet further advantageous feature of the preferred embodiment is that the preferred glow discharge device significantly improves the sensitivity and intensity of generated reagent ions compared with a conventional mass spectrometer.

It is also contemplated that at least some reagents may be used both as a source of reagent ions for Electron Transfer Dissociation (and/or Proton Transfer Reaction) and also as a source of lock mass or reference ions for calibrating the mass spectrometer. Analyte ions generated by the ion source 7 are preferably drawn through the sample cone 8 of the mass spectrometer into the first vacuum chamber 3 of the mass spectrometer which is preferably pumped by a vacuum pump 9. The first vacuum chamber 3 and the inlet into the mass spectrometer are preferably heated. The analyte ion source and initial stages of the mass spectrometer may comprise a z-spray (RTM) ion source.

Figure 2:
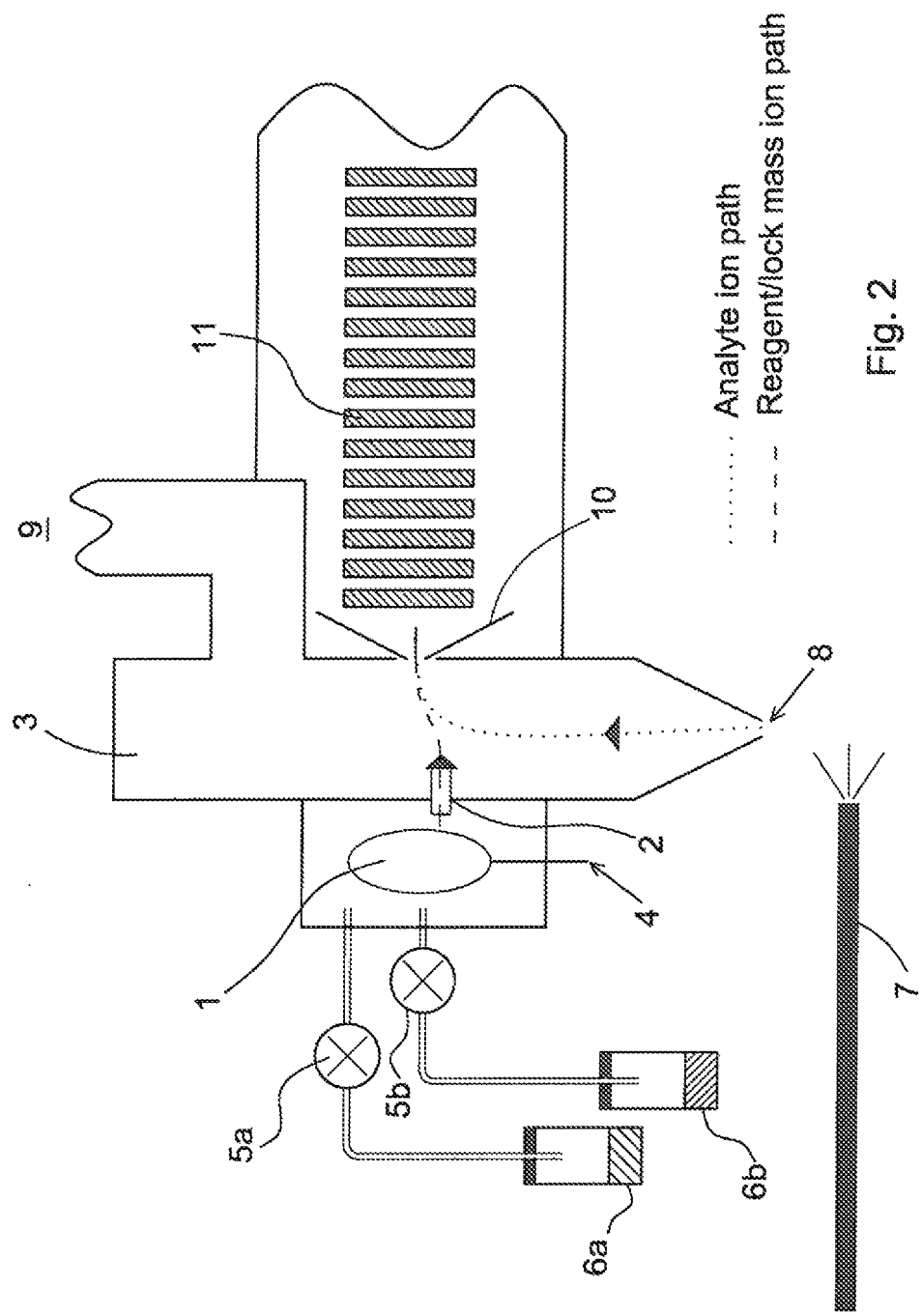
FIG. 2 shows an embodiment of the present invention wherein two reagents may be supplied to the glow discharge ion source which is provided in a housing adjacent to the first vacuum chamber of a mass spectrometer.

FIG. 2 shows another embodiment of the present invention wherein two different reagents 6a,6b may be introduced into the housing in which the glow discharge volume 1 is generated. According to an embodiment one of the reagents 6a may comprise a reagent which is used to generate reagent ions which are used for ion-ion reactions such as Electron Transfer Dissociation. The other reagent 6b may be used to generate calibrant or lock mass ions. The selection of one species of reagent ions is preferably performed or controlled by use of one or more valves or micro-dosing devices 5a,5b. Alternatively, a mass selective device such as a resolving quadrupole rod set mass filter may be arranged or otherwise provided downstream of the glow discharge source 1 in order to filter out any undesired ions and/or to transmit onwardly only desired ions.

Further embodiments are contemplated wherein three, four, five, six or more than six different reagents may be selectively introduced into the housing in which the glow discharge 1 is created. A flow of gas may be admitted towards the discharge volume or otherwise more generally into the housing in which the glow discharge 1 is created. The gas may comprise an inert make up gas which is preferably introduced in order to increase the pressure within the discharge chamber or housing relative to the first vacuum stage or chamber 3. Alternatively, the gas may comprise a chemical ionisation (CI) gas which is preferably provided in order to enhance the ionisation of the reagent in the discharge chamber or housing. The gas may flow past or through the reagent as a means of controlling the flow of reagent neutrals into the glow discharge. The addition of gas into the housing in which the glow discharge 1 is generated in combination with suitable or appropriate differential pumping preferably enables the discharge chamber or housing in which the glow discharge 1 is generated to be interfaced to other vacuum regions of the mass spectrometer.

The first vacuum chamber 3 and the inlet into the mass spectrometer as shown in FIG. 2 may be heated. The analyte ion source and initial stages of the mass spectrometer may comprise a z-spray (RTM) ion source.

Figure 3:
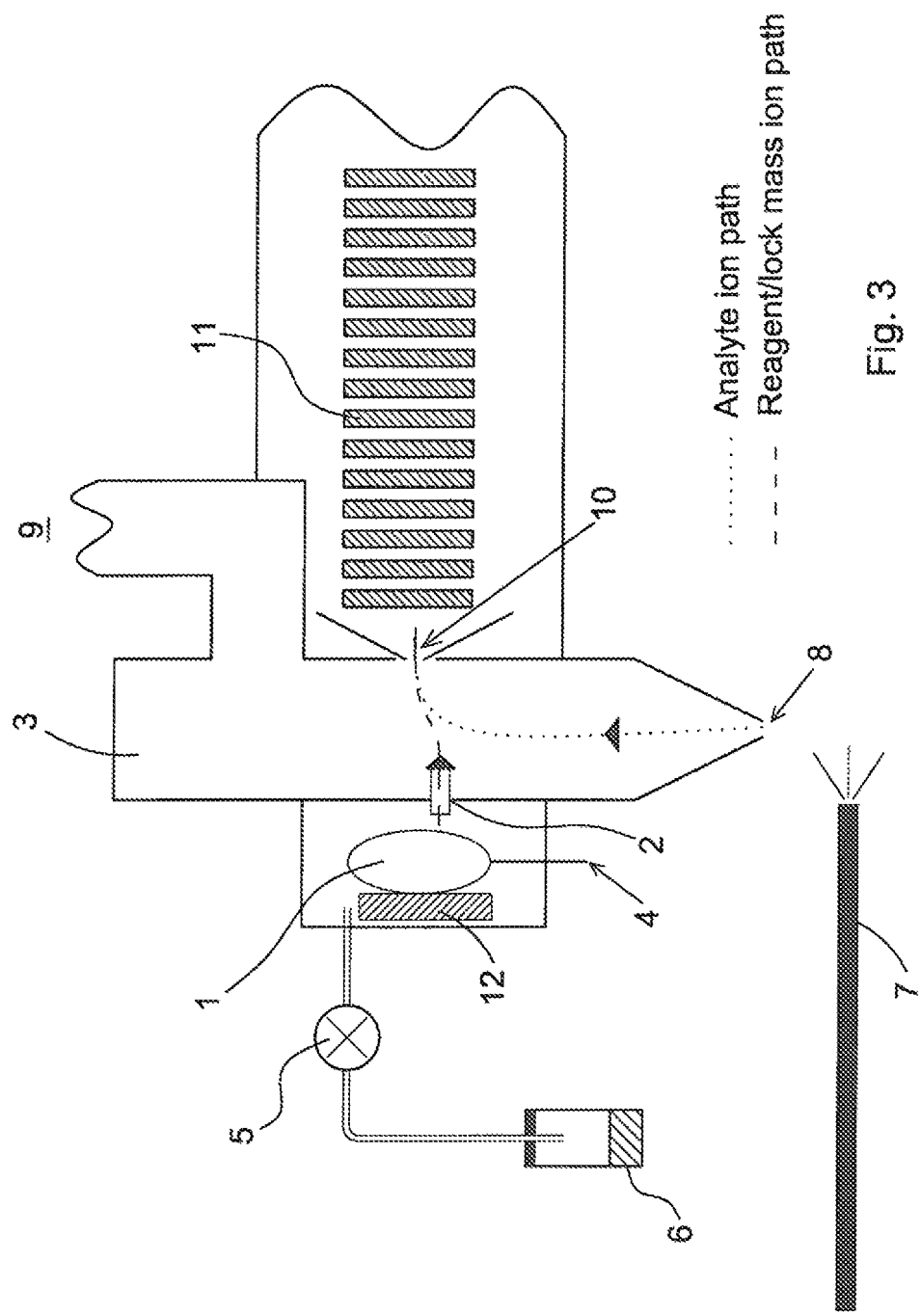
FIG. 3 shows an embodiment of the present invention wherein a solid reagent is provided within a housing adjacent to the first vacuum chamber of the mass spectrometer and wherein part of the solid reagent is ionised by a glow discharge to provide lock mass ions for calibrating the mass spectrometer.

An alternative embodiment for producing lock mass ions is shown in FIG. 3. According to this embodiment a solid highly ionic material 12 such as caesum iodide (CsI) may be placed or located within the housing which is located adjacent to the first vacuum chamber 3 of the mass spectrometer. When a glow discharge 1 is produced within the housing, the glow discharge 1 preferably causes caesium ions to be released from the surface of the caesium iodide block. The caesium ions are preferably sputtered and are preferably extracted from the discharge volume 1 for use as a means of lock mass correction. A reagent introduction system comprising reagent 6, a fluid flow path and a valve 5 may also be provided in order to introduce reagent into the housing. Reagent ions are preferably created by the glow discharge 1 within the housing and may be onwardly transmitted for use as Electron Transfer Dissociation and/or Proton Transfer Reaction reagent ions. Therefore, according to this embodiment both calibrant or lock mass ions and also reagent ions may be generated within the housing and may be onwardly transmitted into the first vacuum stage 3 and subsequent vacuum stages of the mass spectrometer. According to an embodiment a resolving quadrupole rod set mass filter may be provided upstream of an ion-ion reaction cell and downstream of the glow discharge source 1 to ensure that only desired reagent ions (preferably reagent anions) are introduced into the reaction cell. The reagent ions preferably interact with analyte ions (preferably analyte cations) and preferably cause the analyte ions to fragment by means of Electron Transfer Dissociation.

The first vacuum chamber 3 and the inlet into the mass spectrometer shown in FIG. 3 may be heated. The analyte ion source and initial stages of the mass spectrometer may comprise a z-spray (RTM) ion source.

Figure 4:
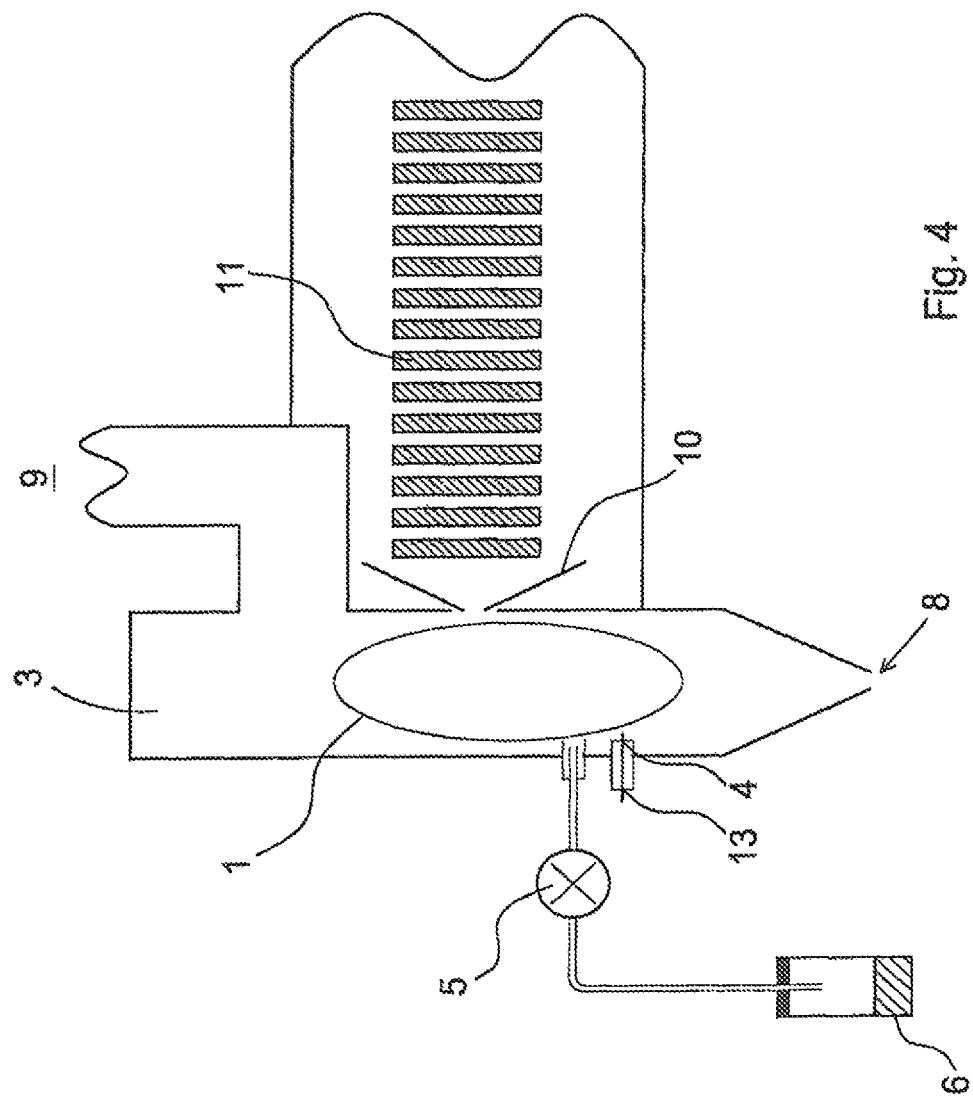
FIG. 4 shows an embodiment of the present invention wherein a glow discharge is initiated directly in the first vacuum chamber of a mass spectrometer and wherein a volatile reagent may be fed into the first vacuum chamber downstream of the electrode which is used to generate the glow discharge.

FIG. 4 shows a further embodiment wherein a glow discharge is initiated directly within the first vacuum region 3 of the mass spectrometer rather than in a housing adjacent to the first vacuum chamber 3. According to the embodiment shown in FIG. 4 a volatile reagent 6 is preferably fed via a valve 5 directly into the first vacuum chamber 3 of the mass spectrometer. The reagent is preferably introduced into the first vacuum chamber 3 at a location downstream of an electrode or pin 4. The electrode or pin 4 is preferably connected via an electrical connection 13 to a high voltage source. A high voltage is preferably applied to the electrode or pin 4 via the electrical connection 13 and this preferably causes a glow discharge to be created within the first vacuum chamber 3.

Other embodiments are contemplated wherein the volatile reagent 6 may be replaced with a solid such as caesium iodide (CsI) which is preferably located within the first vacuum chamber 3. The block of caesium iodide is preferably provided within the first vacuum chamber 3 adjacent the region wherein a glow discharge 1 is formed within the first vacuum chamber 3 by the application of a high voltage to the electrode or pin 4.

The first vacuum chamber 3 and the inlet into the mass spectrometer shown in FIG. 4 may be heated. The analyte ion source and initial stages of the mass spectrometer may comprise a z-spray (RTM) ion source.

Figure 5:
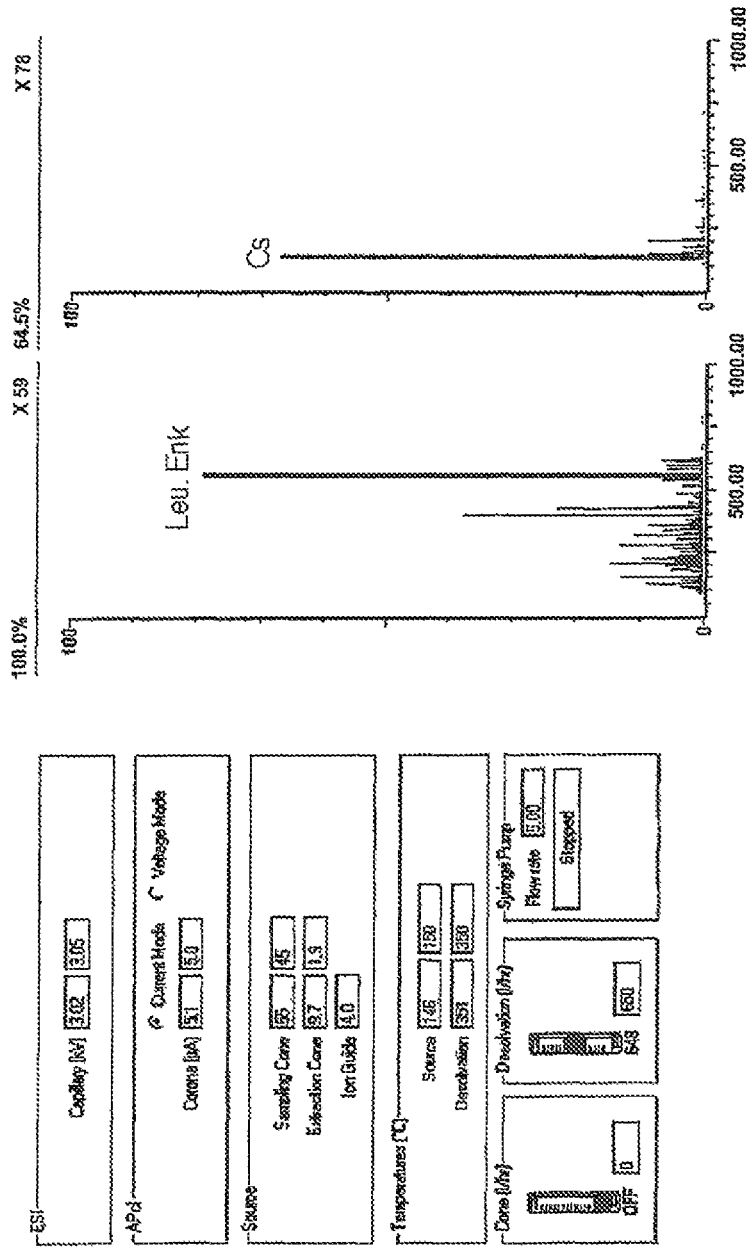
FIG. 5 shows a tune page from a mass spectrometer and shows mass spectra showing caesium lock mass ions generated by a preferred glow discharge ion source and analyte ions of Leucine Enkephalin generated by an Electrospray ion source.

FIG. 5 shows a tune page from a modified Waters Q-T of premier (RTM) mass spectrometer and corresponding mass spectra. The modified mass spectrometer was operated in positive ion mode and was arranged substantially as shown in FIG. 4 except that caesium lock mass ions were generated from a solid block of caesium iodide which was provided within the first vacuum chamber 3 adjacent electrode or pin 4. The glow discharge source 1 was generated using an ESCi (RTM) power supply operating in constant current mode with approximately 5 μA of discharge current at a voltage of approximately +700V. Leucine Enkephalin was used as a test analyte and was ionised by a conventional Electrospray ion source. The corresponding mass spectrum for the test analyte having a mass to charge ratio of 556 is shown in FIG. 5. Caesium lock mass calibration ions having a mass to charge ratio of 133 which were generated by the glow discharge ionising the caesium iodide block were used to calibrate the mass spectrometer. A corresponding mass spectrum showing the caesium lock mass ions is also shown in FIG. 5. Alternating acquisitions of 1 s duration were acquired with an inter-spectrum delay of 0.1 sec.

Figure 6:
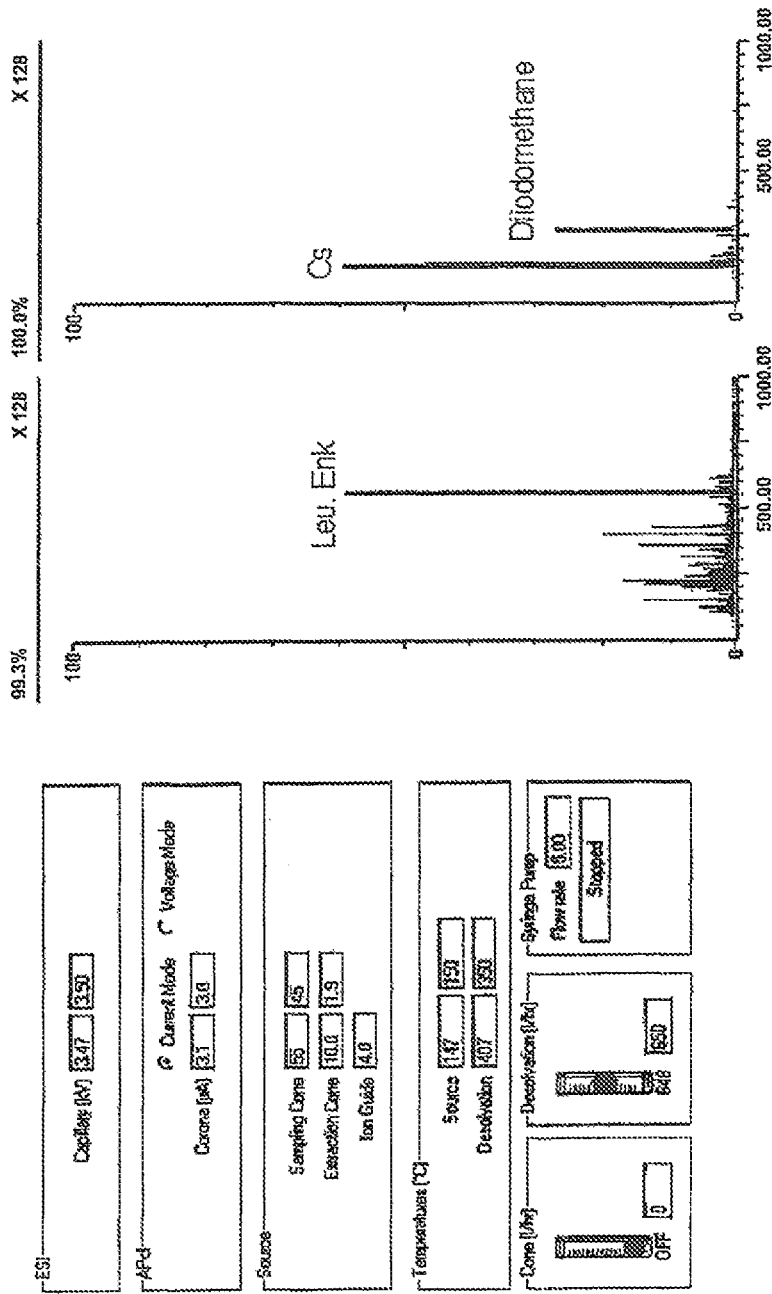
FIG. 6 shows a tune page from a mass spectrometer and shows mass spectra showing caesium and diiodomethane lock mass ions generated by a preferred glow discharge ion source and analyte ions of Leucine Enkephalin generated by an Electrospray ion source.

FIG. 6 shows a further tune page and corresponding mass spectra which were obtained when Diiodomethane vapour was additionally introduced into the mass spectrometer in a manner substantially as shown in FIG. 4 as an additional calibration compound. A block of caesium iodide was also provided within the first vacuum chamber 3 adjacent the glow discharge 1 so that caesium ions were also released as a source of reference ions. Mass spectra for the analyte ions as generated by an Electrospray ion source and the two lock mass ions as generated by a glow discharge device according to an embodiment of the present invention are shown in FIG. 6.

Figure 7:
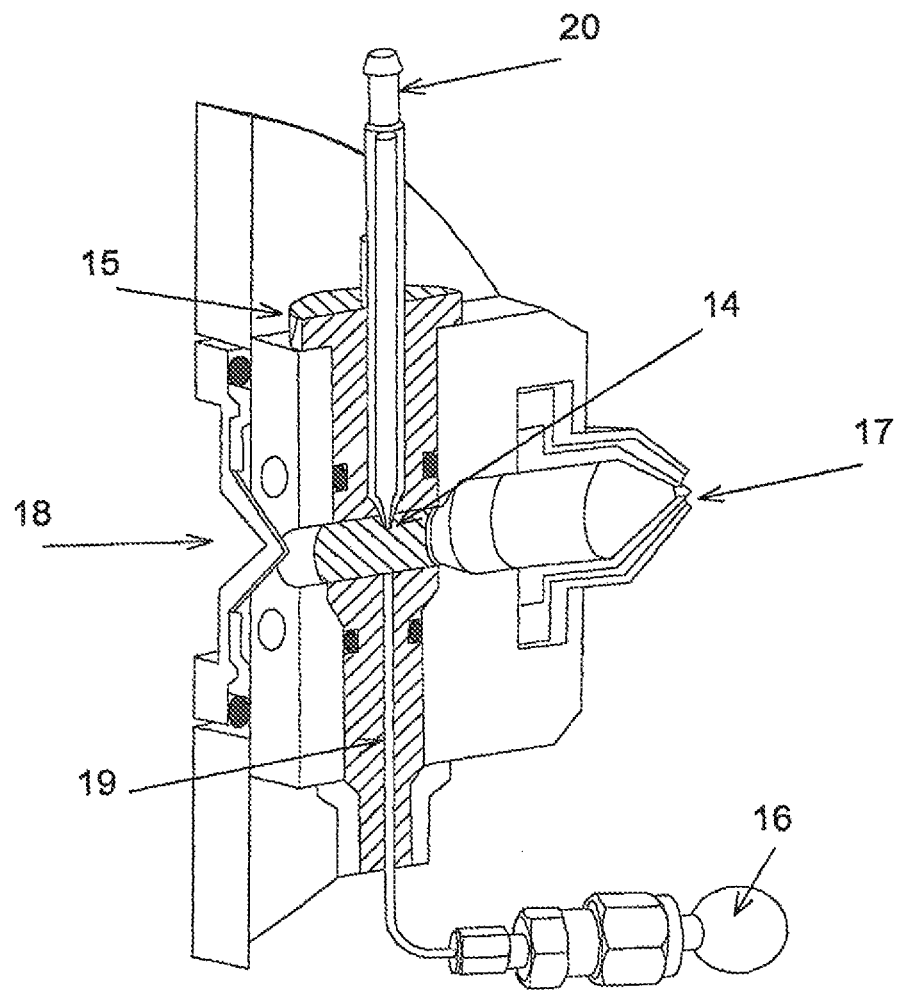
FIG. 7 shows an embodiment wherein a discharge pin for generating a glow discharge is provided within the body of an isolation valve which is located in the first vacuum chamber of a mass spectrometer.

FIG. 7 shows a further embodiment of the present invention wherein a discharge pin 14 is incorporated into an isolation valve 15 located within the first vacuum chamber of the mass spectrometer. The isolation valve 15 is located between a skimmer cone 17 and an extraction cone 18 of the mass spectrometer. The discharge pin 14 preferably comprises a stainless steel capillary tube (0.0625" O.D.×0.5 mm I.D.) which is preferably arranged to have a sharp or pointed end. According to the embodiment shown in FIG. 7 vapour from a reagent cell 16 is preferably emitted via a reagent vapour outlet tube 19 in close proximity to the sharp or pointed end of the discharge pin 14. The reagent cell may comprise a vial of reagent crystals e.g. azobenzene or fluoranthene. It will be understood that the isolation valve 15 has a cylindrical bore or port which when aligned with the central cylindrical bore of the first vacuum chamber 3 allows ions to pass from the analyte sampling cone 17 towards the extraction cone 18 which leads into the second vacuum chamber. However, when the mass spectrometer is not operational the isolation valve may be rotated by 90° so that the cylindrical bore or port of the isolation valve 15 is no longer in alignment with the cylindrical bore of the first vacuum chamber 3. As a result, the isolation valve 15 acts to seal the vacuum chambers of the mass spectrometer from the atmosphere and therefore assists in maintaining a low pressure within the mass spectrometer when the mass spectrometer is not operational. It will be appreciated that maintaining a low pressure within the mass spectrometer significantly reduces the start-up time when operation of the mass spectrometer is desired to be resumed.

According to a preferred embodiment of the present invention the reagent cell may 16 be positioned such that reagent vapour flows down and through the tube which preferably forms the discharge pin 14 and emerges from the tube at the sharp or pointed end of the discharge pin 14. According to an embodiment the reagent cell 16 may comprise a vial of reagent crystals e.g. azobenzene or flourantheene may be provided in solid form within the reagent cell 16 which is preferably connected to the tube. A make-up gas (which is preferably inert) such as nitrogen may also be used. The make-up gas may be arranged to flow past the crystals which may be held at room temperature (~20° C.). The make-up gas may be supplied at a flow rate of around 20 ml/min.

According to the preferred embodiment oxygen is preferably substantially prevented from flowing through the discharge region as this can cause a loss of reagent signal. According to the preferred embodiment the source volume may be purged with nitrogen.

According to an embodiment a voltage of −500 V may be applied to an electrode 20 which is in electrical contact with the discharge pin 14 so that the discharge pin is preferably maintained at a voltage of −500 V in order to generate a glow discharge.

Figure 8:
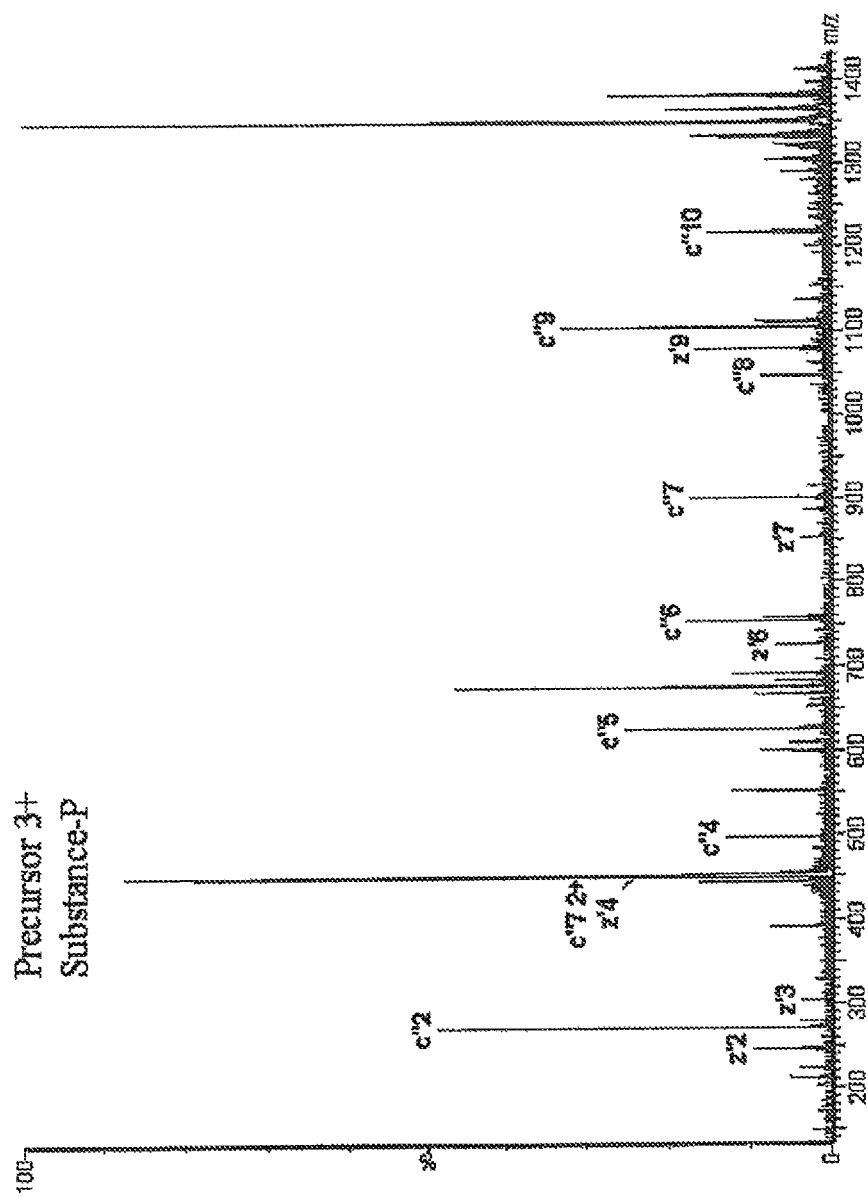
FIG. 8 shows an Electron Transfer Dissociation fragmentation spectrum of triply charged substance-P which has been subjected to fragmentation by azobenzene reagent ions generated by a glow discharge source according to an embodiment of the present invention.

FIG. 8 shows an ETD fragmentation spectrum which was obtained by interacting triply charged substance-P ions with azobenzene reagent anions. The azobenzene reagent anions were formed by introducing azobenzene reagent vapour through a tubular pin 14 located within the isolation valve of a mass spectrometer in a manner substantially as shown in FIG. 7 and as described above. The end of the tubular pin 14 was pointed and formed the glow discharge device. A high voltage was applied to the electrode or pin 14 in order to induce a glow discharge which resulted in the ionisation of the azobenzene vapour to form azobenzene reagent anions. The azobenzene reagent ions when interacted with triply charged substance-P ions in an Electron Transfer Dissociation cell located in a downstream vacuum chamber caused the triply charged substance-P ions to fragment by Electron Transfer Dissociation.

Figure 9A:
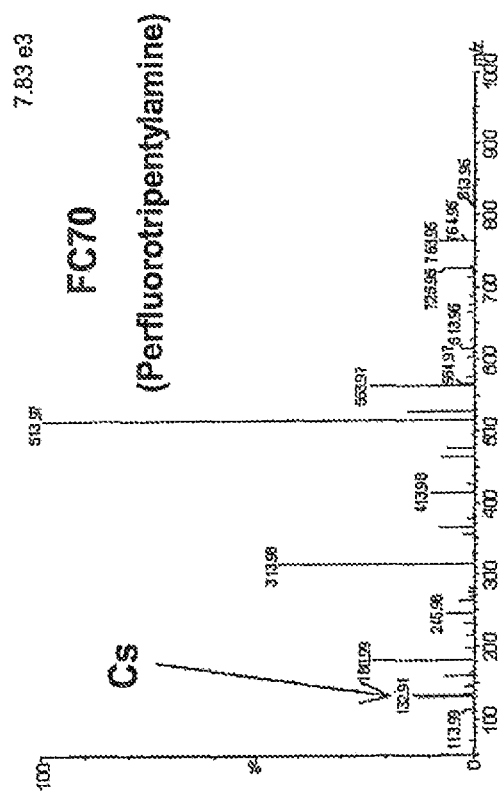
FIG. 9A shows a calibration mass spectrum performed using perfluorotripentylamine (FC70) and caesium ions which were generated by a glow discharge source according to an embodiment of the present invention and FIG. 9B shows an experimental mass spectrum, a reference mass spectrum and a determination of the residual mass errors after calibration.

FIG. 9A shows a mass spectrum obtained according to an embodiment of the present invention wherein calibration was performed using perflourotripentylamine ("FC70") ions and caesium ions. The perfluorotripentylamine ("FC70") ions and caesium ions were generated by introducing perfluorotripentylamine vapour through a tubular pin 14 located within the isolation valve of a mass spectrometer in a manner substantially as shown in FIG. 7 and as described above. The end of the tubular pin 14 was pointed and formed the glow discharge device. A high voltage was applied to the electrode or pin 14 in order to induce a glow discharge which resulted in the ionisation of the perfluorotripentylamine vapour to form perfluorotripentylamine reference ions. The caesium reference ions were generated by coating the region around the end of the tubular pin 14 with caesium iodide.

Other embodiments are contemplated wherein other reagents for calibration/lock mass may be introduced into the glow discharge device including perfluorokerosine ("PFK"), perfluorotrihexylamine, perfluorotributylamine ("FC43"), diiodomethane and iodotetrafluoropropane.

Figure 9B:
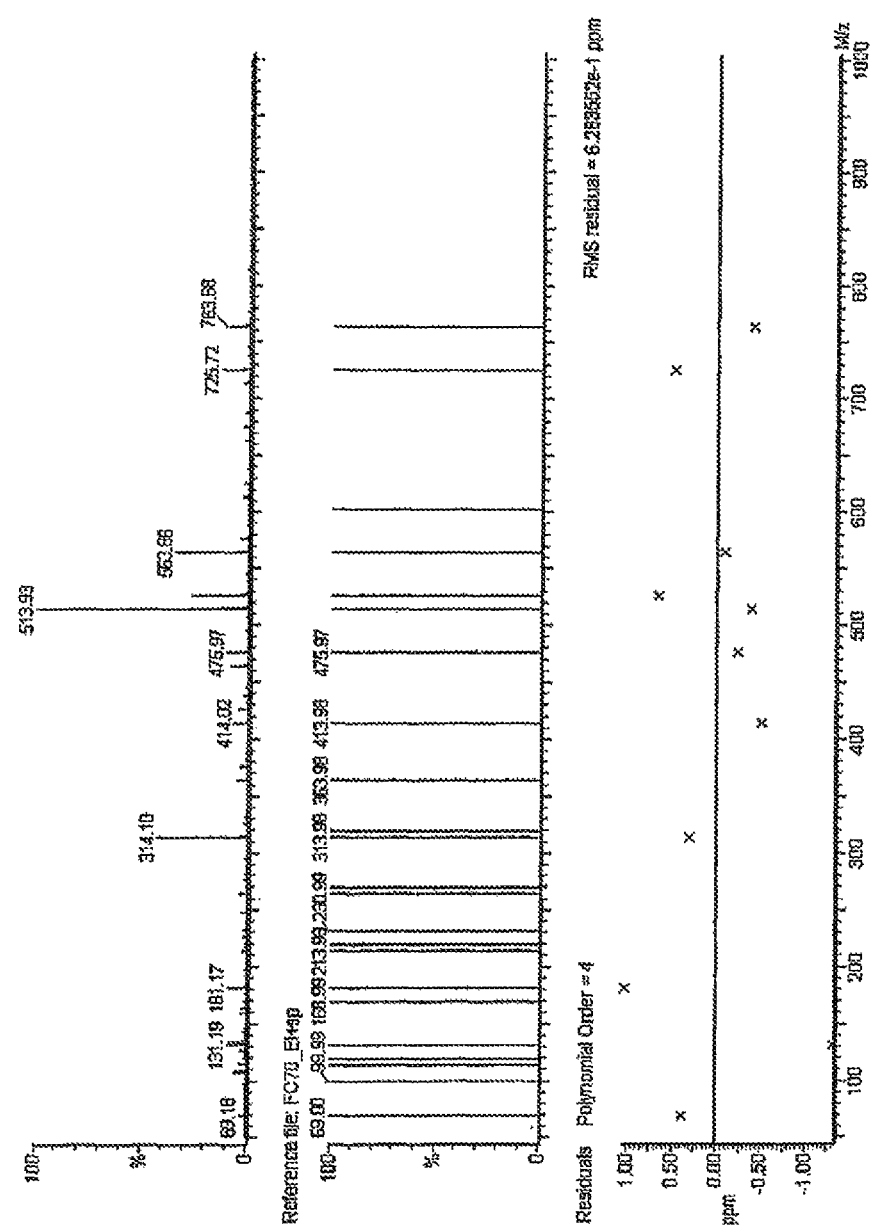

The upper mass spectrum in FIG. 9B shows an nominal mass spectrum obtained from experimental data prior to calibration of the mass spectrometer. The mass or mass to charge ratio values were calculated using an estimated calibration method wherein the mass is proportional to the time of flight squared. Perfluorotripentylamine ("FC70") ions were generated by an Electrospray ionisation ion source and were admitted into the mass spectrometer and were subsequently mass analysed.

The middle mass spectrum shows a reference or theoretical mass spectrum for perfluorotripentylamine and is based upon reference data.

The mass spectrometer was then calibrated more accurately by applying a higher order (fourth order) time of flight polynomial curve to the experimental data. The RMS of the residual errors of the least squares fitting of the fourth order polynomial curve against the experimental data are shown in the lower figure and was determined to be 0.6 ppm.

Although according to the preferred embodiment reagent ions are preferably generated either in a housing adjacent to the first vacuum chamber 3 or alternatively directly in the first vacuum chamber 3, according to other less preferred embodiments reagent ions may be generated in a housing adjacent to a second or subsequent vacuum chamber or alternatively may be generated in a second or subsequent vacuum chamber which is preferably arranged downstream of the first vacuum chamber 3. For example, it is contemplated that a glow discharge ion source may be provided in the same vacuum chamber as an Electron Transfer Dissociation reaction cell and/or the same vacuum chamber as a Proton Transfer Reaction reaction cell.

According to the preferred embodiment of the present invention the glow discharge device comprises a pin or electrode 4,14 to which a DC and/or RF voltage is applied in order to generate a glow discharge 1.

Although the present invention has been described with reference to the preferred embodiments, it will be understood by those skilled in the art that various changes in form and detail may be made to the particular embodiments discussed above without departing from the scope of the invention as set forth in the accompanying claims.

The invention claimed is:

1. A mass spectrometer comprising:
   a vacuum chamber;
   an atmospheric pressure ion source for generating first ions, wherein first ions generated by said atmospheric pressure ion source are transmitted, in use, into said vacuum chamber via a sampling cone or first aperture;
   a glow discharge device for generating second ions, wherein second ions generated by said glow discharge device are either generated within said vacuum chamber or are transmitted into said vacuum chamber without being transmitted through said sampling cone or first aperture; and
   one or more dispensing devices for dispensing one or more reagents in proximity to said glow discharge device so that said one or more reagents are ionised, in use, by a glow discharge caused or generated by said glow discharge device;
   wherein said one or more reagents comprise one or more lock mass or calibration reagents for mass calibrating the mass spectrometer;
   wherein said glow discharge device is housed in a housing adjacent said vacuum chamber and wherein second ions generated by said glow discharge device pass from said housing through a second aperture into said vacuum chamber; and
   wherein an electric field is maintained between said housing and said vacuum chamber in order to urge reagent ions from said housing into said vacuum chamber.

2. The mass spectrometer according to claim 1, wherein said second ions are used to calibrate a mass scale of the mass spectrometer or to correct the calibration of the mass scale of the mass spectrometer.

3. The mass spectrometer according to claim 1, wherein said glow discharge device comprises an electrode or pin and wherein said mass spectrometer further comprises a voltage device for supplying or applying a DC or RF voltage to said electrode or pin in order to cause or generate a glow discharge.

4. The mass spectrometer according to claim 1, further comprising either a solid, powdered, partially solid or gel substance, a volatile liquid or a gas which is arranged or supplied in proximity to said glow discharge device so that ions are sputtered, extracted or released from said substance, liquid or gas.

5. The mass spectrometer according to claim 4, wherein said substance comprises caesium iodide.

6. The mass spectrometer according to claim 1, wherein said lock mass or calibration reagent comprises perfluorotripentylamine ("FC70"), perfluorokerosine ("PFK"), perfluorotrihexylamine, perfluorotributylamine ("FC43"), diiodomethane, iodotetrafluoropropane or fluoranthene.

7. The mass spectrometer according to claim 1, further comprising a supply device for supplying said one or more lock mass or calibration reagents in proximity to said glow discharge device.

8. The mass spectrometer according to claim 1, wherein said glow discharge device comprises a tube having a sharpened or pointed end.

9. The mass spectrometer according to claim 8, further comprising a supply device for supplying said one or more lock mass or calibration reagents through said tube.

10. The mass spectrometer according to claim 1, wherein said glow discharge device is operated in a continuous or pulsed manner.

11. The mass spectrometer according to claim 1, wherein said glow discharge device is maintained or operated in a mode of operation at a potential selected from the group consisting of: (i) <−1 kV; (ii) −900 to −800 V; (iii) −800 to −700 V; (iv) −700 to −600 V; (v) −600 to −500 V; (vi) −500 to −400 V; (vii) −400 to −300 V; (viii) −300 to −200 V; (ix) −200 to −100 V; (x) −100 to 0 V; (xi) 0 to 100 V; (xii) 100 to 200 V; (xiii) 200 to 300 V; (xiv) 300 to 400 V; (xv) 400 to 500 V; (xvi) 500 to 600 V; (xvii) 600 to 700 V; (xviii) 700 to 800 V; (xix) 800 to 900 V; (xx) 900 to 1000 V; and (xxi) >1 kV.

12. The mass spectrometer according to claim 1, wherein said glow discharge device is operated, in use, at a pressure selected from the group consisting of (i) >0.001 mbar; (ii) >0.01 mbar; (iii) >0.1 mbar; (iv) >1 mbar; (v) >10 mbar; (vi) >100 mbar; (vii) <0.001 mbar; (viii) <0.01 mbar; (ix) <0.1 mbar; (x) <1 mbar; (xi) <10 mbar; (xii) <100 mbar; (xiii) 0.001-0.01 mbar; (xiv) 0.01-0.1 mbar; (xiv) 0.1-1 mbar; (xv) 1-10 mbar; (xvi) 10-100 mbar; and (xvii) 0.01-20 mbar.

13. A method of mass spectrometry conducted with a vacuum chamber; an atmospheric pressure ion source for generating first ions; and a glow discharge device for generating second ions, said method comprising:

generating first ions by said atmospheric pressure ion source and transmitting said first ions into said vacuum chamber via a sampling cone or first aperture; and generating second ions by said glow discharge device, wherein said second ions are generated either within said vacuum chamber or are transmitted into said vacuum chamber without being transmitted through said sampling cone or first aperture; and dispensing one or more reagents in proximity to said glow discharge device so that said one or more reagents are ionised by a glow discharge caused or generated by said glow discharge device;

wherein said one or more reagents comprise one or more lock mass or calibration reagents for mass calibrating the mass spectrometer;

wherein said glow discharge device is housed in a housing adjacent said vacuum chamber and wherein second ions generated by said glow discharge device pass from said housing through a second aperture into said vacuum chamber; and wherein said method comprises maintaining an electric field between said housing and said vacuum chamber in order to urge reagent ions from said housing into said vacuum chamber.

\* \* \* \* \*